(12) United States Patent
Kobayashi

(10) Patent No.: US 10,856,486 B2
(45) Date of Patent: Dec. 8, 2020

(54) RIPPLED DOUBLE FLOWERED NEW GUINEA IMPATIENS VARIETIES AND METHOD OF BREEDING THE SAME

(71) Applicant: Dümmen Group B.V., De Lier (NL)

(72) Inventor: Ruth Kobayashi, Encinitas, CA (US)

(73) Assignee: DÜMMEN GROUP B.V., de Lier (NL)

( * ) Notice: Subject to any disclaimer, the term of this patent is extended or adjusted under 35 U.S.C. 154(b) by 484 days.

(21) Appl. No.: 15/489,704

(22) Filed: Apr. 17, 2017

(65) Prior Publication Data

US 2017/0295736 A1    Oct. 19, 2017

Related U.S. Application Data

(60) Provisional application No. 62/323,981, filed on Apr. 18, 2016.

(51) Int. Cl.
    *A01H 6/16*    (2018.01)
    *A01H 5/02*    (2018.01)

(52) U.S. Cl.
    CPC ............ *A01H 6/165* (2018.05); *A01H 5/02* (2013.01)

(58) Field of Classification Search
    CPC .................................... A01H 6/165
    USPC .................................................... Plt./319
    See application file for complete search history.

(56) References Cited

U.S. PATENT DOCUMENTS

| | | |
|---|---|---|
| PP7,130 P | 1/1990 | Simchock |
| PP8,893 P | 9/1994 | Drewlow |
| PP8,907 P | 9/1994 | Drewlow |
| PP8,916 P * | 9/1994 | Drewlow ............... A01H 6/165 Plt./319 |
| 5,399,798 A | 3/1995 | Drewlow et al. |
| 5,684,225 A | 11/1997 | Drewlow et al. |
| 6,353,162 B1 | 3/2002 | Cosner |
| 2005/0177905 A1 | 8/2005 | Sanders |

OTHER PUBLICATIONS

International Search Report and Written Opinion issued in International Application No. PCT/US17/28018, dated Jul. 20, 2017.

* cited by examiner

*Primary Examiner* — David H Kruse
(74) *Attorney, Agent, or Firm* — Parker Highlander, PLLC

(57) ABSTRACT

Provided herein are double flowered New Guinea *Impatiens* cultivars comprising rippled, twisted, incurved petals. Methods for breeding the disclosed *Impatiens* are also provided.

17 Claims, 2 Drawing Sheets

RIPPLED DOUBLE FLOWERED NEW GUINEA IMPATIENS VARIETIES AND METHOD OF BREEDING THE SAME

This application claims the benefit of U.S. Provisional Patent Application No. 62/323,981, filed Apr. 18, 2016, the entirety of which is incorporated herein by reference.

BACKGROUND OF THE INVENTION

1. Field of the Invention

The present embodiments provided herein relate generally to horticultural, plant breeding and plant genetics.

2. Description of Related Art

*Impatiens* has become an increasingly important ornamental crop. In 1970, in order to increase the germplasm pool for this crop, the U.S. Department of Agriculture introduced 23 *Impatiens* from New Guinea, 1 from Celebes and 1 from Java. H. F. Winters, *Am. Hotic.* 52: 923 (1973). New Guinea *Impatiens* (NGI) encompasses a group of interbreeding species that include *I. schlecteri* Warb., *I. herzogii* K. Schum, *I. linearifolia* Warb., *I. mooreana* Schltr., *I. hawkeri* Bull, and other species of the same geographic origin which are interfertile. NGI are diverse phenotypically, producing large flowers with colors ranging from white to various shades of lavender, red, pink and orange. The leaves are of various shapes and sizes, with and without variegations. C. Grey-Wilson, *Kew Bulletin* 34: 661 (1979). Although diverse phenotypically, members of NGI are interfertile and generally have a 2n chromosome number of 32, T. Arisumi, *J. Hered.,* 64: 77 (1973).

Most NGI cultivars typically produce flowers with 5 petals per flower (single flowered). The breeding of NGI cultivars which produce one or more flowers having at least seven petals per flower has been developed (U.S. Pat. Nos. 5,399,798 and 5,684,225). The typical phenotype of both single and double flowering NGIs have petals that are presented horizontally.

SUMMARY OF THE INVENTION

In a first embodiment of the invention there is provided a New Guinea *Impatiens* plant comprising at least one flower with a rippled, double, flower phenotype wherein the plant is obtained by introgression of the rippled flower trait from a plant grown from the seed deposited at NCIMB under the accession no. 42566, said plant having been selected for a rippled, double flower phenotype. In some aspects, substantially all the flowers produced by said plant comprise the rippled, double, flower phenotype. In certain aspects, the plant may additionally comprise at least one horticultural elite trait. For example, the horticultural elite trait may be selected from short stature, upright growth, strong branches, large blooms, vigorous growth, disease resistance, insect resistance, herbicide tolerance, increased longevity, increased period of flowering, drought tolerance, uniform plant habit, a desired leaf color, a desired morphology, or flowers with desirable colors. In additional aspects, the plant comprises leaves that are medium green, dark green or variegated green. In further aspects, plants may comprise flowers that are white, lavender, red, pink or orange, or a combination thereof.

In a further embodiment there is provided a progeny plant of a New Guinea *Impatiens* in accordance with the embodiments and aspects described herein, said progeny plant having a rippled, double, flower phenotype.

Yet a further embodiment of the invention provides a tissue culture of regenerable cells of the New Guinea *Impatiens* plant of any of the embodiments and aspects described herein. In certain aspects, the regenerable cells are from embryos, meristematic cells, pollen, leaves, petals, roots, root tips, anther, pistil, seed or stem. In further embodiments there is provided a plant part of the New Guinea *Impatiens* plant of any of the embodiments and aspects described herein. In some aspects, the part is a seed, a stalk, a petal, a bud, a leaf or a root. In additional aspects, said part can be regenerated into a plant comprising a rippled, double flower phenotype.

In yet still a further embodiment there is provided a method of producing a New Guinea *Impatiens* plant comprising crossing a plant of the embodiments and aspects described herein with a second New Guinea *Impatiens* plant and selecting a progeny plant comprising the rippled, double flower phenotype. In specific aspects, the second New Guinea *Impatiens* plant may comprise at least a first horticulturally elite trait. In further aspects, the method additionally comprises selecting a progeny plant comprising the rippled, double flower phenotype and the first horticulturally elite trait.

Still yet a further embodiment of the invention provides a method for obtaining a New Guinea *Impatiens* plant according to the embodiments and aspects described herein comprising the step of introgression of the rippled, double flower trait from a plant grown from the seed deposited at NCIMB under the accession no. 42566. Further embodiments provide a New Guinea *Impatiens* seed wherein, upon growth, the seed produces a plant having a rippled, double, flower phenotype and comprises a trait that was introgressed from a plant grown from the seed deposited at NCIMB under the accession no. 42566.

As used herein in the specification and claims, "a" or "an" may mean one or more. As used herein in the specification and claims, when used in conjunction with the word "comprising", the words "a" or "an" may mean one or more than one. As used herein, in the specification and claims, "another" or "a further" may mean at least a second or more.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Embodiments

Figure 1A:
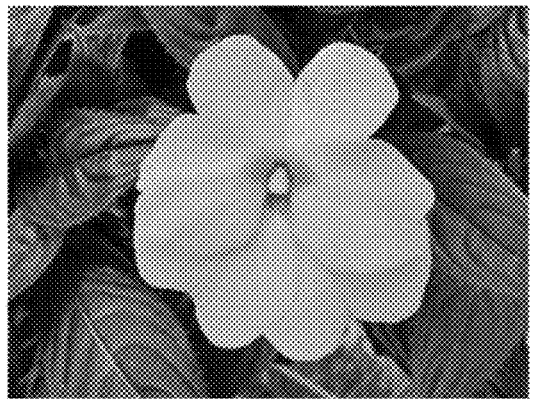
FIGS. 1A-1D—1A depicts a typical single NGI flower with five petals presented horizontally. 1B depicts a typical double NGI flower which has at least 7 full or partial petals presented horizontally. 1C-1D depict semi-double NGI flowers with a sixth full petal that is incurved.
Figure 1B:
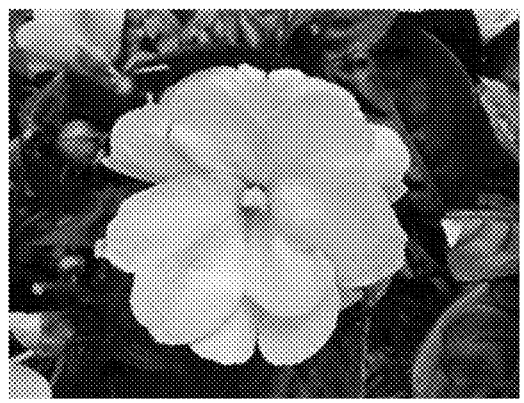
Figure 1C:
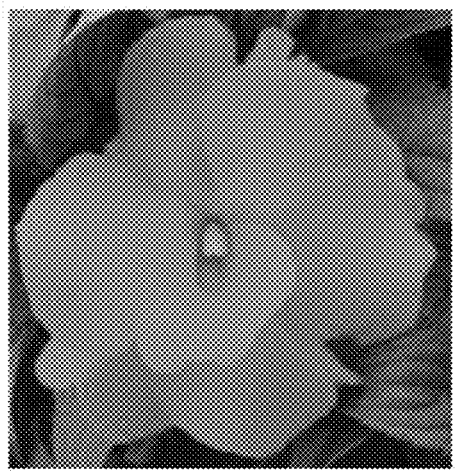
Figure 1D:
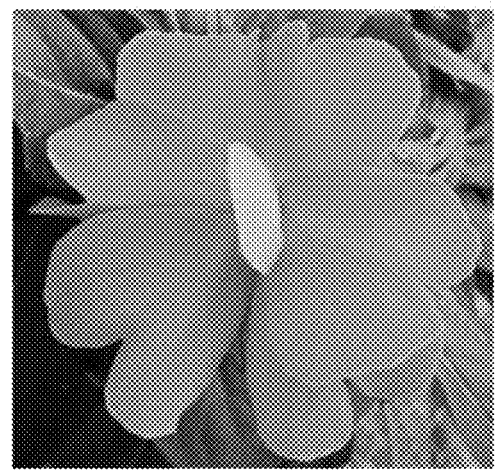
Figure 2A:
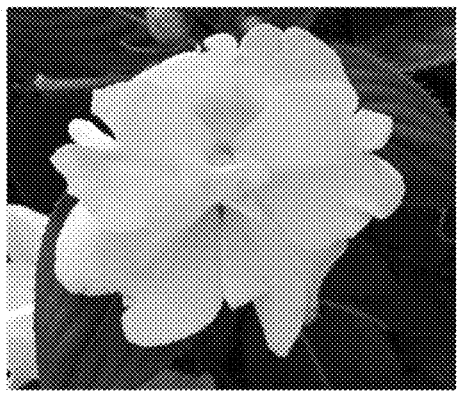
FIGS. 2A-2C depict double NGI flowers with rippled (2A), twisted (2B), or incurved (2C) petals.
Figure 2B:
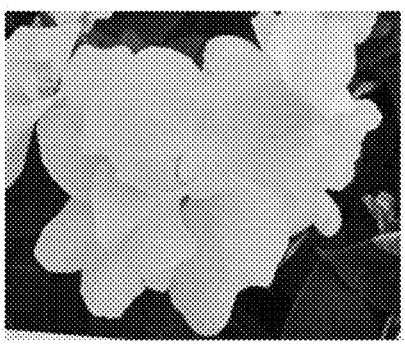
Figure 2C:

In populations of seedlings from crosses between double flowering genotypes with single flowering genotypes a novel semi-double phenotype having incurved petals was discovered (FIGS. 1A-1D). By further intercrossing incurved petal genotypes to double flowering genotypes and single flowering genotypes, a double flowered plant with rippled, twisted, incurved petals were developed (FIGS. 2A-2C). Plants comprising the rippled, double flower, phenotype, such as cultivar NN14-701012, can be used to introgress the rippled flower phenotype into other horticulturally elite NGI lines and to generate plants with any desired flower color. Thus, the NGI plants provided herein can serve as basis for an entire class of new NGI plants that produce aesthetically pleasing rippled, double flowers.

II. Definitions

As used herein, "single", "single-type", or "singleness" are each defined as the typical New Guinea *Impatiens* (NGI) plant which produces flowers having five petals per flower or the typical NGI flower which has five petals.

As used herein, "semi-double", "semi-double-type", or "semi-doubleness" are each defined as a NGI plant which produces one or more flowers having a sixth full or partial petal per flower or a NGI flower which has a sixth full or partial petal.

As used herein, "double", "double-type", "double-flowering", or "doubleness" are each defined as a NGI plant which produces one or more flowers having at least 7 full or partial petals per flower or a NGI flower which has at least 7 full or partial petals. Double-flowering NGI cultivars are genetically stable. Double-flowering cultivars can be stably reproduced by means of asexual propagation. The characteristic of doubleness can be predictably bred into diverse single-type and semi-double-type NGI genetic backgrounds.

As used herein, the "degree of doubleness per flower" is defined as a measure of the number of extra full or partial petals per flower produced beyond the number five normally found on NGI cultivars. The greater the degree of doubleness per flower, the greater the number of full or partial petals produced per flower.

As used herein, the "degree of doubleness per plant" is defined as a measure of the number of flowers per plant which have at least 7 petals per flower. The greater the degree of doubleness per plant, the higher is the percentage of total flowers produced by the plant which have at least 7 full or partial petals per flower. As already noted, double-type NGI cultivars are genetically stable, as evidenced by the stability of the trait through both asexual propagation and sexual crosses. Depending upon the cultivar, however, the degree of doubleness per flower or plant may be adversely affected by environmental stress factors, without any variance in the genotype of the plant. Environmental stress factors which adversely affect flowering of NGI plants generally, such as high temperatures, low soil fertility or water stress, may adversely affect the degree of doubleness per flower or plant. Most notably, the degree of doubleness per flower or plant may decline with increasing temperatures, especially in the range of 30° C. and above. NGI cultivars have been successfully selected, as reported herein, in which the degree of doubleness per flower or plant is not greatly affected by high temperature. Among cultivars in which the degree of doubleness per flower or plant is adversely affected by temperature, however, the degree of doubleness is restored with removal of the environmental stress factor(s) (see, e.g., U.S. Pat. Nos. 5,399,798 and 5,684,225, each of which is incorporated herein by reference).

Rippled and wavy flower petal margins—As used herein a rippled flower phenotype refers to a plant having at least one flower having 1, 2, 3, 4, 5, 6, 7 of more full or partial twisted, or incurved petals with rippled, wavy and/or notched margins per flower. Flower petal presentation stays somewhat cupped, notched margins may interlock allowing the flower to maintain its rosette appearance. Inner petals are often smaller than primary petals. Incurved petals remain at less than a 90 degree angle (e.g., less than a 85, 80, 75, 70, 65, 60, 55, 50, or 45 degree angle) from pedicel. Petal presentation a full flower maturity remains 3 dimensional, rather than flat open flower petal presentation of most NGI. In preferred aspects, a plant having as rippled flower phenotype further comprises a double flower phenotype.

Horticultural elite—Plants exhibiting desired horticultural traits are considered to be horticultural elite, viz. genetic traits. Traits that may be considered to confer elitism good longevity, large flowers, brilliant color, tolerance to pests, tolerance to disease, long flowering time, and the like.

Genetic transformation—A process of introducing a DNA molecules (e.g., a vector or expression cassette) into a cell or protoplast in which that exogenous DNA is incorporated into a chromosome or is capable of autonomous replication.

Introgression—The process of transferring a genetic trait (e.g., a rippled flower phenotype) from one genotype to another.

III. Deposit Information

A representative deposit of 1,100 seeds from rippled double flowered NGI plants from NN14-701012 has been made with the National Collections of Industrial, Food and Marine Bacteria (NCIMB), 23 St. Machar Drive, Aberdeen AB2 1RY, Scotland, United Kingdom on Mar. 30, 2016. Those deposited seeds have been assigned Accession No. NCIMB 42566. An additional deposit of seeds to bring the total number to 2,500 seeds from rippled double flowered NGI plants from NN14-701012 was made and accepted on Feb. 7, 2017, under the same accession number. They were tested on Mar. 17, 2017, and found to be viable.

The foregoing deposits were made in accordance with the terms and provisions of the Budapest Treaty relating to deposit of microorganisms and were made for a term of at least thirty (30) years and at least five (05) years after the most recent request for the furnishing of a sample of the deposits is received by the depository, or for the effective term of the patent, whichever is longer, and will be replaced if it becomes non-viable during that period.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Breeding of Double Flowered NGI Plants with Rippled, Twisted, Incurved Petals NGI cultivar NN14-701012 was developed, which comprise novel esthetically pleasing flower phenotypes. In particular, the plants have a double flower phenotype and include flowers have petals that have at least partially irregular, notched, rippled or wavy margins, and are twisted, or incurved. Overall petal presentation stays somewhat cupped, notched margins may interlock allowing the flower to maintain its rosette appearance. Inner petals often remain smaller than primary petals. Normal NGI flowers have 5 petals that open flat (perpendicular to the pedicel). NN14-701012 was produced by crossing *Impatiens hawkeri* 'NN-0013' with Male parent *Impatiens hawkeri* 'NN-1339'. Approximately 5% to 10% of the progeny from this cross expressed at least 6 petals with partially rippled petal margins and/or incurved petals. A seed deposit of NN14-701012 has been made at NCIMB. Thus, NGI plants having a rippled and/or wavy double flower phenotype can be produced by growing seeds from NN14-701012 and selecting plants having the rippled flower phenotype. Likewise, the phenotype can be introgressed from this line into any desired NGI cultivar, such a horticulturally elite line or an line having desired flower color. Foliage and plant growth habit are similar to other standard, commercially available New Guinea *Impatiens*.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,399,798
U.S. Pat. No. 5,684,225
H. F. Winters, *Am. Hotic.* 52: 923 (1973).
C. Grey-Wilson, *Kew Bulletin* 34: 661 (1979)
T. Arisumi, *J. Hered.*, 64: 77 (1973).

What is claimed is:

1. A New Guinea *Impatiens* plant comprising at least one flower with a rippled, double, flower phenotype wherein the plant is obtained by introgression of the rippled flower trait from a plant grown from the seed deposited at NCIMB under the accession no. 42566, said plant having been selected for a rippled, double flower phenotype.

2. The New Guinea *Impatiens* plant according to claim 1 wherein all the flowers produced by said plant comprise the rippled, double, flower phenotype.

3. The New Guinea *Impatiens* plant of claim 1, further comprising at least one horticultural elite trait.

4. The New Guinea *Impatiens* plant according to claim 3, wherein said horticultural elite trait is selected from short stature, upright growth, strong branches, large blooms, vigorous growth, disease resistance, insect resistance, herbicide tolerance, increased longevity, increased period of flowering, drought tolerance, uniform plant habit, a desired leaf color, a desired morphology, or flowers with desirable colors.

5. The New Guinea *Impatiens* plant of claim 1, comprising leaves that are medium green, dark green or variegated green.

6. The New Guinea *Impatiens* plant of claim 1, comprising flowers that are white, lavender, red, pink or orange, or a combination thereof.

7. A progeny plant of the New Guinea *Impatiens* in accordance with claim 1, said progeny plant having a rippled, double, flower phenotype.

8. A tissue culture of regenerable cells of the New Guinea *Impatiens* plant of claim 1.

9. The tissue culture of claim 8, wherein the regenerable cells are from embryos, meristematic cells, pollen, leaves, petals, roots, root tips, anther, pistil, seed or stem.

10. A plant part of the New Guinea *Impatiens* plant of claim 1.

11. The plant part of claim 10, wherein the part is a seed, a stalk, a petal, a bud, a leaf or a root.

12. The plant part of claim 10, wherein said part can be regenerated into a plant comprising a rippled, double flower phenotype.

13. A method of producing New Guinea *Impatiens* plant comprising crossing a plant of claim 1 with a second New Guinea *Impatiens* plant and selecting a progeny plant comprising the rippled, double flower phenotype.

14. The method of claim 13, wherein the second New Guinea *Impatiens* plant comprises at least a first horticulturally elite trait.

15. The method of claim 14, further comprising selecting a progeny plant comprising the rippled, double flower phenotype and the first horticulturally elite trait.

16. A method for obtaining a New Guinea *Impatiens* plant according to claim 1 comprising the step of introgression of the rippled, double flower trait from a plant grown from the seed deposited at NCIMB under the accession no. 42566.

17. A New Guinea *Impatiens* seed produced by cultivating a New Guinea *Impatiens* plant obtained by the method of claim 16.

* * * * *